United States Patent [19]
Bixler et al.

[11] Patent Number: 6,045,780
[45] Date of Patent: Apr. 4, 2000

[54] TOOTHPASTE COMPOSITION

[75] Inventors: Harris J. Bixler, Northport, Me.; Grecilda Sanchez-Zaballero, Mandaue, Philippines

[73] Assignee: Shemberg Marketing Corporation, Cebu, Philippines

[21] Appl. No.: 09/102,444

[22] Filed: Jun. 22, 1998

[51] Int. Cl.$^7$ ...................................................... A61K 7/16
[52] U.S. Cl. ...................................................... 424/49
[58] Field of Search ................................. 424/49–58

[56] References Cited

U.S. PATENT DOCUMENTS

| | | |
|---|---|---|
| 2,839,448 | 6/1958 | Hager et al. . |
| 4,029,760 | 6/1977 | De Roeck born Holtzhaeur et al. ............................................................................ 424/49 |
| 4,048,300 | 9/1977 | Tomlinson et al. . |
| 4,081,526 | 3/1978 | Asakawa et al. ........................ 424/57 |
| 4,282,204 | 8/1981 | Phillips et al. ............................ 424/49 |
| 4,308,253 | 12/1981 | Schmid et al. ............................ 424/54 |
| 4,344,931 | 8/1982 | Aguilar .................................... 424/52 |
| 4,374,823 | 2/1983 | Harvey et al. ............................ 424/52 |
| 4,453,979 | 6/1984 | DeMasi et al. ........................... 424/49 |
| 4,702,905 | 10/1987 | Mithchell et al. ......................... 424/49 |
| 4,716,036 | 12/1987 | Schelm .................................... 424/57 |
| 4,828,833 | 5/1989 | Cordon .................................... 424/49 |
| 4,855,128 | 8/1989 | Lynch et al. .............................. 424/49 |
| 5,030,444 | 7/1991 | Hoyles et al. ............................ 424/49 |
| 5,096,698 | 3/1992 | Mitchell et al. . |
| 5,225,177 | 7/1993 | Wason et al. . |
| 5,240,710 | 8/1993 | Bar-Shalom et al. . |
| 5,279,815 | 1/1994 | Wason et al. . |
| 5,571,502 | 11/1996 | Winston et al. . |
| 5,624,906 | 4/1997 | Vermeer . |
| 5,670,138 | 9/1997 | Venema et al. . |

*Primary Examiner*—Shep K. Rose
*Attorney, Agent, or Firm*—Kevin M. Farrell

[57] ABSTRACT

Disclosed is a toothpaste composition comprising ultra low viscosity guar and carrageenan as a combination viscosity builder. In preferred embodiments of the toothpaste composition the combination viscosity builder comprises less than about 10% of the toothpaste composition by weight, and more preferably, about 0.5% to about 5% of the toothpaste composition by weight. The low viscosity guar preferably comprises less than about 50% of the combination viscosity builder by weight, and more preferably, about 20% to about 30% of the combination viscosity builder by weight. Also disclosed is a dry blend comprising about 20–30% low viscosity guar, about 50–60% iota-type carrageenan and about 20–30% lambda-type carrageenan. The specifications which relate to these components of the dry blend are identical to those discussed above in connection with the toothpaste composition. The dry blend, when appropriately hydrated, has a water viscosity of at least about 40 cps.

18 Claims, 4 Drawing Sheets

TOOTHPASTE COMPOSITION

BACKGROUND OF THE INVENTION

Carrageenan is a linear-sulfated polysaccharide of D-galactose and 3,6 anhydro-D-galactose (3.6 AG) which is extracted from red seaweed (Rhodophyceae). Commercially available carrageenans are essentially ground, dehydrated gels containing approximately 12% water. These materials can viscosity or gel a system into which they are incorporated. Rheological properties of the carrageenan depend upon the nature and quantity of the carrageenan, as well as the inclusion of other components (particularly salts and polyols) in the formulation.

Carrageenan has been used as a toothpaste binder, but its application is limited due to the fact that the cost of this ingredient is relatively high as compared with alternative binders. For example, CMC (carboxymethyl cellulose) is a reagent which can be used instead of carrageenan as a toothpaste binder. In bulk, the cost of CMC is less than ½ the cost of the carrageenan reagent.

In tropical areas, however, a cellulase enzyme attacks CMC. This results in an undesirable decrease in the viscosity of the toothpaste which can become watery. Thus, in tropical countries, particularly those referred to as developing countries, toothpaste producers are forced to use the more expensive carrageenan binding reagent, or an equally expensive alternative such as xanthan, or run the danger of offering the consumer an inferior product. A less expensive alternative to carrageenan as a toothpaste binder which is not subject to the viscosity breakdown of CMC is highly desirable to the producers of toothpaste.

SUMMARY OF THE INVENTION

In one aspect, the present invention relates to a cellulase-resistant toothpaste composition comprising ultra low viscosity guar and carrageenan as a combination viscosity builder. Because ultra low viscosity guar is less expensive than carrageenan, the combination offers cost saving potential. In preferred embodiments of the toothpaste composition the combination viscosity builder comprises less than about 10% of the toothpaste composition by weight, and more preferably, about 0.5% to about 5% of the toothpaste composition by weight. The low viscosity guar preferably comprises less than about 50% of the combination viscosity builder by weight, and more preferably, about 20% to about 30% of the combination viscosity builder by weight.

Formulations wherein the carrageenan component comprises a mixture of iota and lambda carrageenan types yield excellent results. The preferred iota carrageenan type is produced as an approximately 100 mesh size calcium salt or mixed calcium and sodium salt (greater than 95% through a 100 mesh screen). The preferred lambda carrageenan type is produced as an approximately 100 mesh size sodium salt. A toothpaste produced according to present specification will have a toothpaste viscosity rating of between about 20–35 BKU (Brookfield helipath viscometer). The strength of the paste as determined by the Cuban rating will be between 6 and 9.

The present invention also relates to a dry blend comprising about 20–30% low viscosity guar, about 50–60% iota-type carrageenan and about 20–30% lambda-type carrageenan. The specifications which relate to these components of the dry blend are identical to those discussed above in connection with the toothpaste composition. The dry blend, when appropriately hydrated, has a water viscosity of at least about 40 cps (1.5% dry blend in distilled water at 75° C.)

DETAILED DESCRIPTION OF THE INVENTION

Figure 1:
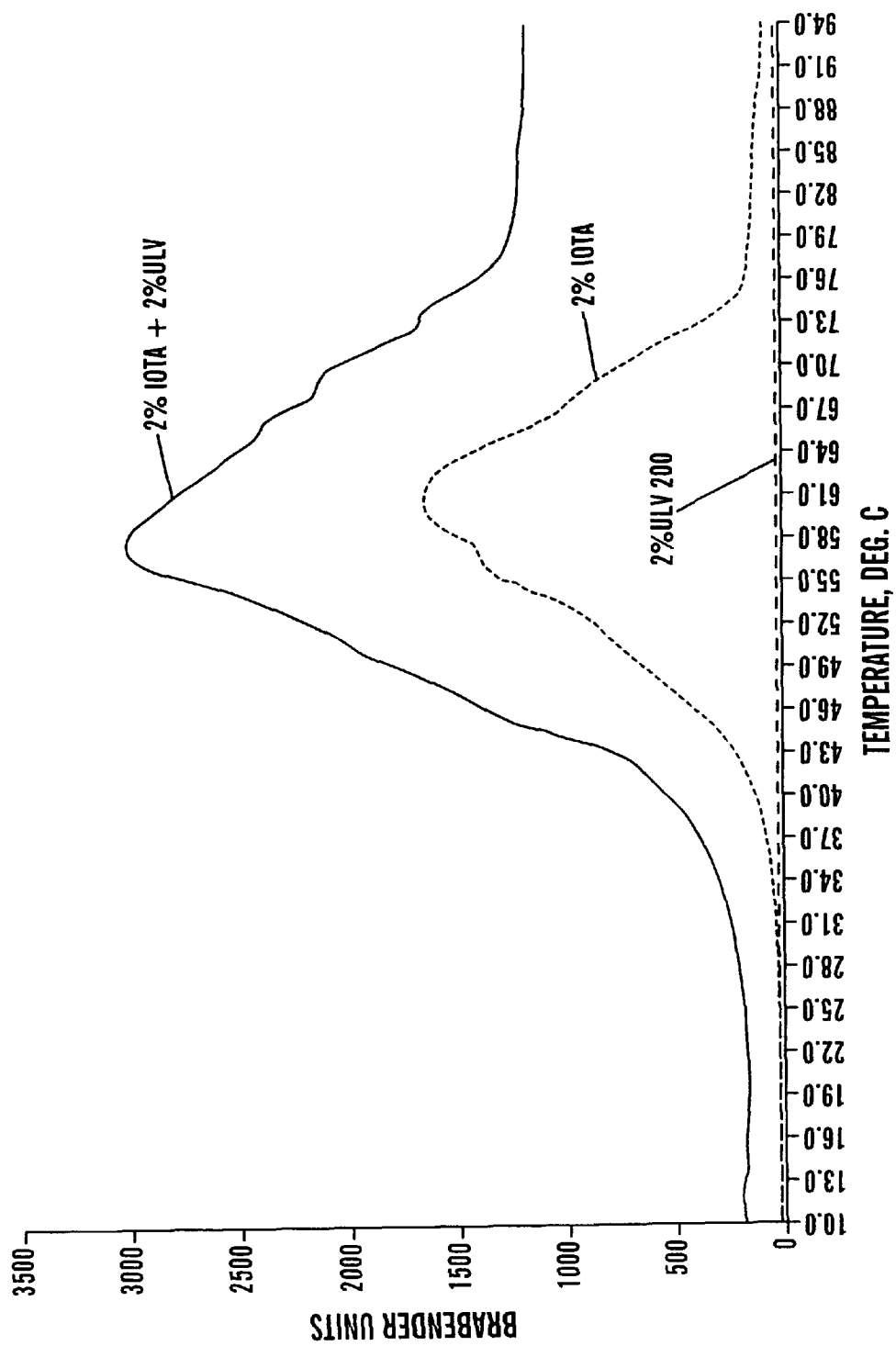
FIG. 1 is a diagrammatic representation of a hydration profile determination for 1) ULV guar (2% ULV 200), 2) 2% iota carrageenan (2% iota), and 3) 2% iota carrageenan and 2% ULV guar (2% iota+2% ULV) in a solution comprising 1:1 water:glycerin, 1% NaCl.

The solid and liquid components in toothpaste compositions are formulated in such a way that the end product is an extrudable creamy mass. The total liquid content in toothpaste is typically about 20–75% by weight of the formulation. Toothpastes generally contain the following components: an abrasive, such as dicalcium phosphate or chalk (calcium carbonate); a humectant such as glycerine, sorbitol, or polyethylene glycol 600; water between 20–35%; salts; sweetener (e.g. sodium saccharine); color and flavor oil; and a binding reagent. Binding reagents are included in a toothpaste composition to build viscosity. Natural and synthetic gums and gum-like materials have been used as binding agents, including, for example, Irish moss (carrageenan), gum guar, gum tragacanth, carboxymethyl cellulose, hydroxyethyl cellulose, polyvinyl pyrrolidone, starch, xanthan, or water-soluble hydrophilic colloidal polymers and synthetic inorganic silicated clays. The binder content typically employed is in an amount up to about 10% by weight, and preferably about 0.5–5% of the formulation. Toothpaste compositions are discussed generally in U.S. Pat. Nos. 4,048,300; 2,839,448; 5,614,175; 5,279,815; 5,225,177; 4,828,833; 5,670,138; 5,096,698; 5,571,502; 5,240,710; and 5,624,906, the disclosures of which are incorporated herein by reference.

The present invention relates to a toothpaste composition comprising Ultra Low Viscosity (ULV) guar gum and carrageenan as a combination viscosity builder. As discussed above, the combination viscosity builder preferably comprises less than about 10% of the toothpaste composition by weight, the most preferred range being from about 0.5% to about 5% of the toothpaste composition by weight.

ULV guar gum is derived from a highly purified extract of Guar seeds "*Cyanopsis tetragonolobus*", a plant native to India. ULV guar gum is a cold water soluble polysaccharide galactommanans, having a mannose to galactose ratio of approximately 2:1. Typically, the molecular weight of native gum guar is in the 180,000 to 220,000 range. Normal guar gum has excessive viscosity and a gummy texture which precludes its use in many food products and toothpaste. The development of ultra low viscosity guar gum allows for its use in products previously limited to using other hydrocolloids. ULV guar gum is highly depolymerized and the molecular weight is substantially lower than that of the native compound. Depolymerization is typically effected through a thermal and mechanical degradation technique. Useful natural features of the guar gum are retained through this process. For example, no detectable etherification or esterification takes place so cold water solubility is retained.

In preferred embodiments, the ultra low viscosity guar used as a component of the combination viscosity builder has a water viscosity rating of from about 200 cps to about 500 cps, the most preferred ULV guar viscosity being about 200 cps and the powder is approximately 100 mesh size. Viscosity determinations on guar are conventionally made using a viscometer, such as a Brookfield viscometer at a gum concentration of 1.5% in water at 25° C.

As previously mentioned, the carrageenans comprise a family of linear sulfated food grade polysaccharides isolated from red seaweeds or marine algae. Carrageenans have been used in toothpaste compositions world-wide for more than 50 years. There are three major carrageenan types (kappa, iota and lambda), all having the ability to build viscosity, with kappa and iota able to form a variety of gels. The various members of the carrageenan family differ from one another in 3,6-anhydro-D-galactose content and the number and position of ester sulfate groups. Carrageenans are highly negatively charged and are isolated as salts (e.g., ammonium, calcium, potassium, and sodium salts). The chemical and structural properties of carrageenans can be exploited in toothpaste to provide a continuous phase gel matrix thereby enhancing viscosity stabilization and providing emulsion stability by trapping additives such as abrasives and flavor oils. Specific interactions between carrageenan and the surface of abrasives both disperse and stabilize solids preventing hardening, caking, and drying out.

The mixture of carrageenan types used affects paste viscosity, paste strength, and paste consistency. With respect to the carrageenan component of the combination viscosity builder, preferred embodiments comprise a blend of iota and lambda carrageenan types which yield a smooth, soft paste which is preferred by consumers. The characteristics of the carrageenan varieties which are relevant in this application are shown in Table 1.

| Carrageenan Type | Relevant Characteristics |
| --- | --- |
| Kappa | yields strong, brittle gel in water and milk solutions |
| Iota | yields weak elastic gel in water and milk solutions |
| Lambda | cold soluble; provides viscosity but does not gel in water and milk solutions |

At present all commercially available lambda carrageenan preparations contain a certain amount of a very weak gelling kappa carrageenan (kappa-2). When used in toothpaste formulations, this lambda/kappa-2 combination behaves similarly to a pure lambda carrageenan preparation.

In preferred embodiments, the iota and lambda carrageenans used in connection with the present invention are isolated and prepared using conventional techniques. It is further preferred that the iota variety be prepared as a calcium salt or a mixture of sodium and calcium salts, to control its hydration and limit its reactivity with the abrasive of choice, either dicalcium phosphate or chalk. It is further preferred that the lambda variety be prepared as a sodium salt to enhance its cold hydration. Alternative salts of carrageenan have been tested but determined to be less well suited for toothpaste applications. Toothpaste formulations contain various amounts of fluorides, phosphates, benzoate, sulfates, and saccharin with their respective cations. Because the ionic environment created by these salts can influence the carrageenan performance as a binder, the cation form of the iota and lambda carrageenans must be carefully selected and controlled. For example, a sodium salt of iota carrageenan has been tested in a toothpaste application. It was determined that the sodium iota carrageenan tended to produce a toothpaste that hardened with time because mobile calcium ions present in the abrasive (either dicalcium phosphate or chalk) gradually displaced the sodium ions of sodium iota carrageenan, converting it to the stronger gelling calcium iota carrageenan salt.

The iota and lambda forms of carrageenan are prepared by conventional techniques. For example, the lambda variety is prepared as the sodium salt from Chilean red marine algae, e.g. *Gigartina radula* and *Gigartina skottsbergii*. The Canadian red marine algae *Chondrus crispus*, or Irish moss, can be substituted for the Chilean marine algae, albeit at a penalty of higher cost. On a commercial scale, the algae is harvested, cleaned, dried, baled and shipped to a processing plant. At the plant, the harvested algae is washed, macerated and extracted in a hot alkaline solution (in this case sodium hydroxide). The mix is then filtered through a filter-press which removes cellulose and other insolubles from the carrageenan solution. The product solution is then neutralized with dilute hydrochloric acid and concentrated by either drum-drying or through alcohol precipitation which removes soluble color bodies and some inorganic salts. The concentrated carrageenan is dried, ground and sieved through a sizing screen.

The calcium salt of the iota variety is prepared from the *Eucheuma spinosum* variety of red marine algae using a similar protocol where calcium hydroxide (lime) is used as the alkaline extraction medium rather than sodium hydroxide.

Preferably the sizing screen used to sieve the carrageenan preparations is 100 mesh. Carrageenan preparations sieved through less than 100 mesh screening yield a product which is overly course for the application in that a "lumpy" paste results. Sieving through a sizing screen of more than 100 mesh results in a product which is overly fine and which tends to result in a dusty environment in the formulation facility.

A variety of alternative formulations incorporating the combination viscosity builder of the present invention are suitable and two examples of specific compositions, each utilizing one of the two common abrasives (dicalcium phosphate and chalk), are shown below:

Formulation I

| | |
| --- | --- |
| Glycerine | 22.00% |
| Dicalcium phosphate | 49.00% |
| Sodium lauryl sulfate | 2.00% |
| Sodium saccharin | 0.20% |
| Sodium benzoate | 0.50% |
| Sodium monofluorophosphate | 0.75% |
| Tetrasodium pyrophosphate | 0.25% |
| Combination viscosity builder | 0.60 to 1.00% |
| Color and flavor oil | to suit |
| Water | to 100.00% |

The Formulation I composition can be prepared on a small scale by dispersing a dry blend of the sodium saccharin, sodium benzoate, tetrasodium pyropyosphate, sodium monofluorophosphate, and combination viscosity builder into a beaker containing the glycerine. This is mixed for 5 minutes and then water is added. The mixture is heated to 65–71° C. in a boiling water bath and the temperature held for 20 minutes, compensating for evaporated water loss. The mixture is then transferred to a Ross mixer. The dicalcium phosphate is added, using a spatula. The formulation is then mixed at speed 2 for 2 minutes, when the mixer is stopped and the bowl and blades are scraped. Mixing is resumed at speed 5–6 for 15 minutes with a vacuum of not less than 28 inches Hg. The sodium lauryl sulfate and flavor oil are then added with mixing at speed 2 for 3 minutes under vacuum. One skilled in the art can easily scale up the protocol described above to commercial scale using no more than routine experimentation.

Formulation II

| Sorbitol | 27.00% |
|---|---|
| Chalk | 42.00% |
| Sodium lauryl sulfate | 1.50% |
| Sodium saccharin | 0.20% |
| Sodium benzoate | 0.50% |
| Sodium monofluorophosphate | 0.76% |
| Tetrasodium pyrophosphate | 0.25% |
| Combination viscosity builder | 0.60 to 1.00% |
| Color and flavor oil | to suit |
| Water | to 100.00% |

The Formulation II composition can be prepared by heating the water to 65° C., and dispersing the combination viscosity builder into the water with stirring while gradually increasing stir speed to high, mixing for 10 minutes. Sorbitol is then added and mixed at medium speed for 15 minutes. A dry blend of sodium saccharin, tetrasodium pyrophosphate, monofluorophosphate, and sodium benzoate is slowly added to the mixture. The mixture is heated to 65–71° C. with stirring at medium to high speed for 15 minutes in a boiling water bath, compensating for water lost to evaporation. The mixture is transferred to a Ross mixer, the chalk is added and mixed for 5 minutes at speed 3. The mixer is stopped and the bowl and blades are scraped before further mixing for 20 minutes at speed 5 with a vacuum of not less than 28 inches Hg. The sodium lauryl sulfate and flavor oils are added and mixed in for 5 minutes at speed 3 under vacuum. As discussed above in connection with Formulation I, scale up is a matter of routine experimentation.

Following formulation, aliquots may be analyzed for quality control purposes. For example, the toothpaste compositions of the present mixture has an overall viscosity rating from about 20 BKU to about 35 BKU (Brookfield helipath units).

Brookfield toothpaste viscosity ratings are determined by the following procedure using Brookfield equipment manufactured by Brookfield Engineering Laboratories, Stoughton, Mass. The equipment includes a Brookfield RVT dial viscometer, a Brookfield Helipath Stand, and a Brookfield RV T-bar Spindle set. To measure viscosity the viscometer is securely mounted on the helipath stand and leveled. A speed setting of 5 rpm and spindle #E are used. Toothpaste samples are measured at room temperature either in the tube or in a beaker. In brief, sample material is centered from ¼ to ½ inch below the spindle tip, and the helipath switch and the motor of the viscometer are turned on. The timer is started when cream contact is made and the dial reading rises above zero—run time is 1.5 minutes. The average reading of the viscometer over the run is taken.

The toothpaste compositions of the present invention also are characterized as having a Cuban rating from about 6 to about 9. Cuban ratings are determined using a Cuban tester, a standardized nozzle, and the paste under evaluation at room temperature. The tube of cream is held one to three inches above the tester and squeezed firmly to start the flow. The tube is passed evenly over the tester from end to end at a moderate speed (2–4 seconds), and timing begins when the cream ribbon touches the end opposite the one from which the ribbon started. Consistency is determined by counting the intervals in which the cream is unbroken after 30 seconds for each ribbon and taking their average. Ten seconds after the start of the stop watch a second ribbon is extruded and timed after it reaches the opposite end of the tester. Care must be taken to prevent the cream ribbons from forming large loops between the bars. This can be accompanied by increasing the speed at which the cream is moved over the tester.

Experiments of the type described in the Exemplification section which follows have revealed an unexpected hydration synergy resulting from the ULV guar/carrageenan combination viscosity builder. This hydration synergy was observed using a Brabender viscograph. The equipment and procedures are discussed in greater detail in the Exemplification section which follows. Without this synergy ULV guar would not be an acceptable component of a viscosity builder in toothpaste. More specifically, a Brabender unit determination for 2% ULV 200 alone was essentially 0. The hydration profile for 2% iota carrageenan alone peaked at about 1,700 Brabender units. However, the hydration profile for the 2% iota carrageenan/2% ULV guar exhibited substantial hydration synergy, peaking at about 3,200 Brabender units. The hydration profile for the 2% lambda carrageenan/2% ULV guar also exhibited substantial hydration synergy, peaking at about 2,800 Brabender units, compared to 2% lambda carrageenan alone whose synergy peaked at around 900 Brabender units, shown in FIG. 2. A control experiment provides no indication of hydration synergy between carrageenan/silica combination viscosity builder (see FIG. 3). The viscosity peak generated from the combination of carrageenan and silica is essentially additive of the peaks generated by two independent components.

In another aspect, the present invention relates to a dry blend comprising about 20–30% low viscosity guar, about 50–60% iota-type carrageenan and about 20–30% lambda-type carrageenan. The specification relating to these components of the dry blend are identical to those discussed above in connection with the combination viscosity builder. The dry blend will typically be sold in bulk to companies engaged in toothpaste formulation. When a water solution viscosity is taken for purposes of quality control, the dry blend has a Brookfield water viscosity rating of at least about 40 cps. Water viscosity is measured by the following procedure: 6 grams of sample is slowly dispersed into a beaker of 394 ml distilled water, with constant stirring. The weight of the beaker plus contents are determined. The solution is heated to 80° C. with constant stirring and the temperature is maintained for 10 minutes. The beaker is reweighed and the resulting weight loss is compensated for by the addition of hot water. The solution is stirred and the temperature lowered until it reaches 75° C., where the viscosity is read with a preheated spindle. For a typical all carrageenan toothpaste viscosity builder (60% iota carrageenan, 40% lambda carrageenan) the water viscosity is 40 to 80 cps.

EXEMPLIFICATION

Hydration Synergy

The experimental series described below was designed to monitor hydration effects using the combination binder of the present invention. Hydration effects were determined using a Brabender Viscograph. More specifically, the instrument employed was a VISCO/AMYLO/GRAPH model VA-VE PT-100 gelation viscometer, equipped with mechanical torque recorder, measuring bowl with stirrer and water cooled cover, and an electronic controller allowing for the evaluation of standard and complex tests of starch and starch-like products. The instrument stores up to five separate temperature programs, each consisting of a ramp, peak temperature, and a hold period. The heating and cooling rates of the instrument are 0.1° C. to 4° C./min. The instrument also offers variable speed control up to 150 rpm. Digital display of actual temperature, temperature rate, hold time, program status and rpm are provided. An interchangeable sensitivity cartridge is also provided. The Brabender Viscograph is an excellent instrument for investigating the swelling and dissolution characteristics of hydrocolloids. Information gathered from the Brabender Viscograph has been shown to characterize the physical properties required by a toothpaste viscosity builder for production, and for finished product simulation of a toothpaste.

For a well-dispersed system, temperature and cation concentration essentially control the rate and extent of carrageenan hydration. For a carrageenan dispersed in a given electrolyte, viscosity can be empirically related to hydration and swelling. During the swelling phase, viscosity increases to a maximum and then falls as the gum dissolves. Salts depress gum swelling and increase the temperature required for functionality (Tye, R.; Carrageenan Hydration and Use, Proceeding of the Third International Gum Conference, Elsevier Applied Science Publishers, Amsterdam (1983)). Most applications in the food industry involve fairly low salt levels and processing temperatures with swelling occurring during cooking. In such systems, the hydration characteristic of the gum is critical to heat transfer during cooking and to performance in the finished food. The functionality of a carrageenan in a dentifrice preparation is also critically dependent on the hydration characteristic of the gum and the concentration and nature of the cations, as well as the type and concentration of humectant (usually a polyol). Hydration determinations should be made in an ionic environment which reflects the application (in this case, toothpaste).

In a given ionic environment, the hydration of a carrageenan is determined by the gel potential of the carrageenan and the particle morphology. Brabender hydration is a sensitive method for detecting changes in both gel potential and particle morphology. The gel strength determination, frequently used to characterize carrageenans, can not detect changes in particle morphology or ease of hydration.

Hydration profiles were determined for guar/carrageenan and a silica/carrageenan control. The protocol employed for hydration determination was as follows. Using the specific toothpaste formulation described earlier, total ion concentration (e.g., sodium, potassium or calcium) used in the preparation of elixir (a term of art used in connection with dentifrice preparations referring to a gum/humectant/salt system prepared prior to abrasive addition) was calculated. If a salt was added with or after the addition of abrasives, the additional salt was not included in the calculation since the additional salt was added only after the binder had been allowed to swell in the manufacturing process.

In the experiments described herein, 1% NaCl was employed to simulate the ionic composition of the toothpaste formulation used herein. The solution was prepared using 250 g distilled water at 10° C. 250 grams of the polyol glycerin was added to the solution. This polyol to water ratio is approximately that of the toothpaste formulation herein.

10 grams of hydrocolloid was dispersed into the water/polyol/salt solution and the resulting mixture was transferred to the Brabender bowl. A plastic spatula was used to scrape the sides of the beaker clean. It is critical that thorough dispersion is achieved. The bowl was fit to the instrument and the run begun with the bowl rotating at 75 rpm and run a thermal ramp of 1.5° C./minute in a 750 gram cartridge. The characterization continued from 10° C. to 95° C. A 20 minute stabilization time was provided at 10° C. prior to the start of heating.

FIG. 1 is a chart showing the hydration profiles of ULV-200 guar, calcium salt of iota carrageenan (CI-100) and CI-100/ULV guar. The hydration profiles shown in FIG. 1 were generated using the following compositions:

| ULV-200 guar | CI-100 | CI-100/ULV 200 |
| --- | --- | --- |
| 250 g dist. water | 250 g dist. water | 240 g dist. water |
| 250 g glycerin | 250 g glycerin | 240 g glycerin |
| 5 g NaCl | 5 g NaCl | 5 g NaCl |
| 10 g ULV 200 | 10 9 CI-100 | 10 g CI-100 |
|  |  | 10 g ULV-200 |

Figure 2:
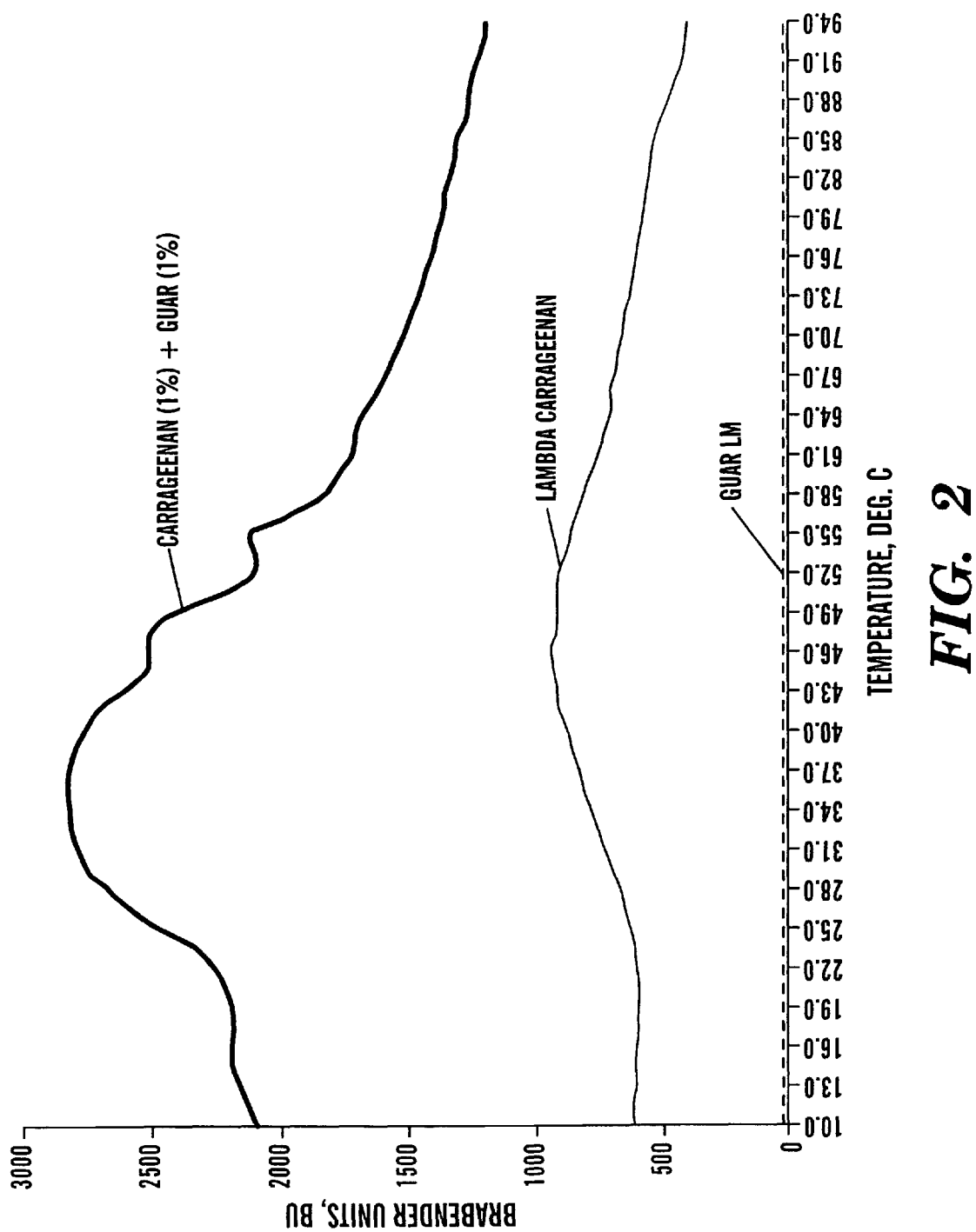
FIG. 2 is a diagrammatic representation of a hydration profile determination for 1) ULV guar (guar LM), 2) lambda carrageenan, and 3) 1% lambda carrageenan and 1% ULV guar in a solution comprising 1:1 water:glycerin, 1% NaCl.

FIG. 2 is a chart showing the hydration profiles of ULV-200 guar, sodium salt of lambda carrageenan (SL-100) and SL-100/ULV guar. The hydration profiles shown in FIG. 2 were generated using the following compositions:

| ULV-200 guar | SL-100 | SL-100/ULV 200 |
| --- | --- | --- |
| 250 g dist. water | 250 g dist. water | 240 g dist. water |
| 250 g glycerin | 250 g glycerin | 240 g glycerin |
| 5 g NaCl | 5 g NaCl | 5 g NaCl |
| 10 g ULV 200 | 10 g SL-100 | 10 g SL-100 |
|  |  | 10 g ULV-200 |

Figure 3:
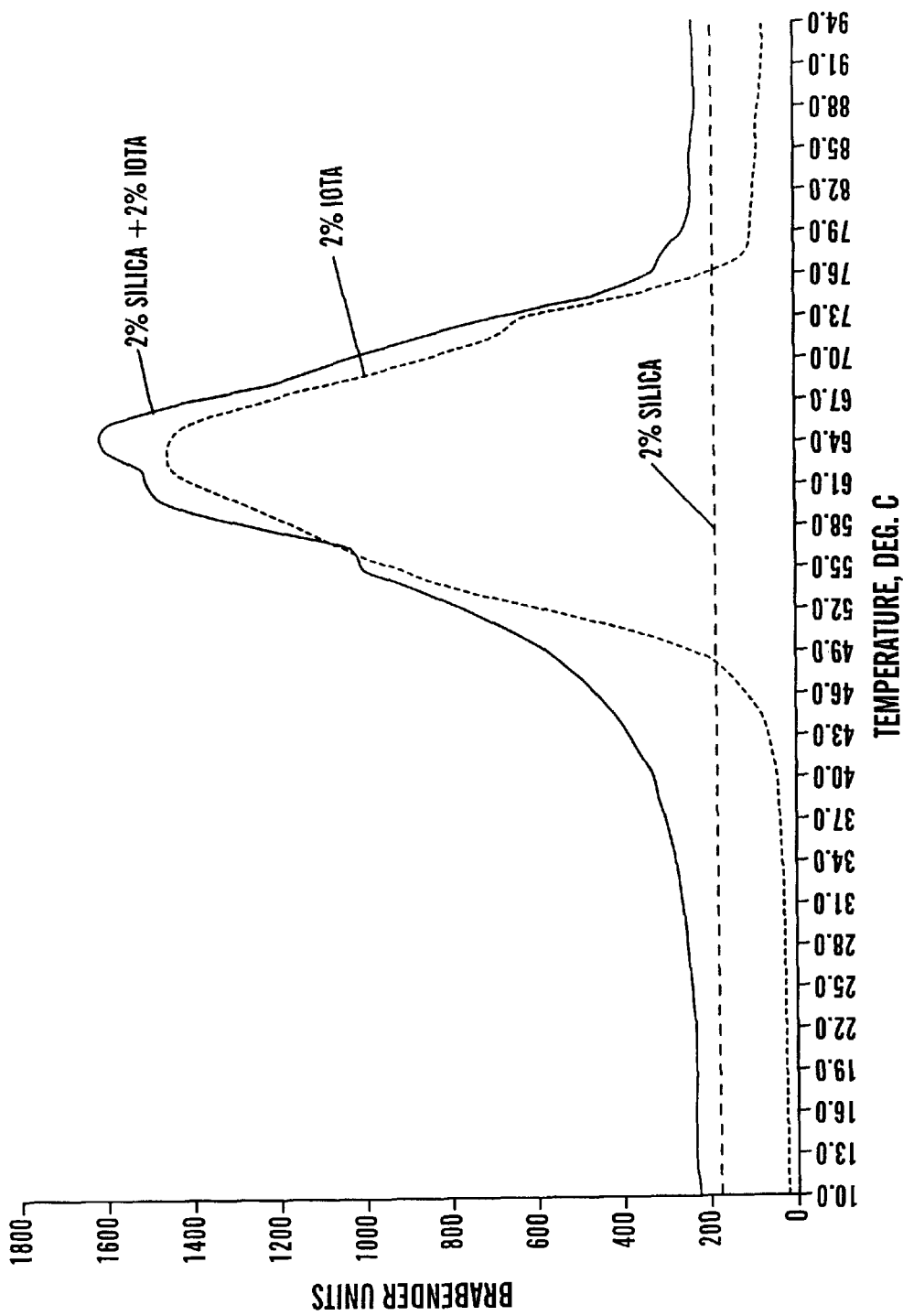
FIG. 3 is a diagrammatic representation of a hydration profile determination for 1) 2% silica, 2) 2% silica and 2% iota carrageenan, and 3) 2% iota carrageenan in a solution comprising 1:1 water:glycerin, 1% NaCl.

FIG. 3 is a chart showing the hydration profiles for the calcium salt of iota carrageenan (CI-100), silica, and a CI-100/silica combination formulation. The hydration profiles shown in FIG. 3 were generated using the following compositions:

| Silica (Zeodent 115) | CI-100 | CI-100/Silica |
| --- | --- | --- |
| 250 g dist. water | 250 g dist. water | 240 g dist. water |
| 250 g glycerin | 250 g glycerin | 240 g glycerin |
| 5 g NaCl | 5 g NaCl | 5 g NaCl |
| 10 g silica | 10 g CI-100 | 10 g CI-100 |
|  |  | 10 g silica |

The hydration data in FIG. 1 clearly shows hydration synergy with iota carrageenan and ULV guar. More specifically, a Brabender unit determination for 2% ULV 200 alone was essentially 0. The hydration profile for 2% iota alone peaked at about 1,700 Brabender units. However, the hydration profile for the 2% iota/2% ULV guar exhibited substantial hydration synergy, peaking at about 3,200 Brabender units.

Similar hydration synergy occurs with lambda carrageenan and ULV guar, demonstrated in FIG. 2. As previously shown, the Brabender unit determination for 2% ULV 200 was essentially 0. The hydration profile for 2% lambda alone peaked at about 900 Brabender units, while the hydration profile for the 2% lambda/2% ULV guar exhibited substantial hydration synergy, peaking at about 2,800 Brabender units.

The hydration synergy seen with carrageenan occurs specifically with the binding reagent ULV guar and was not seen when the alternate binding reagent silica was used in place of ULV guar. For example, FIG. 3 provides no indication of hydration synergy between iota carrageenan and silica. Silica alone and iota alone generated viscosity peaks of about 180 bu and 1450 bu respectively. The combination of silica and iota produced merely an additive effect on viscosity, peaking at about 1640 bu, rather than the synergistic effect seen with ULV-guar and iota-carrageenan. In other experiments the combination of lambda carrageenan and silica also failed to exhibit synergy.

Figure 4:
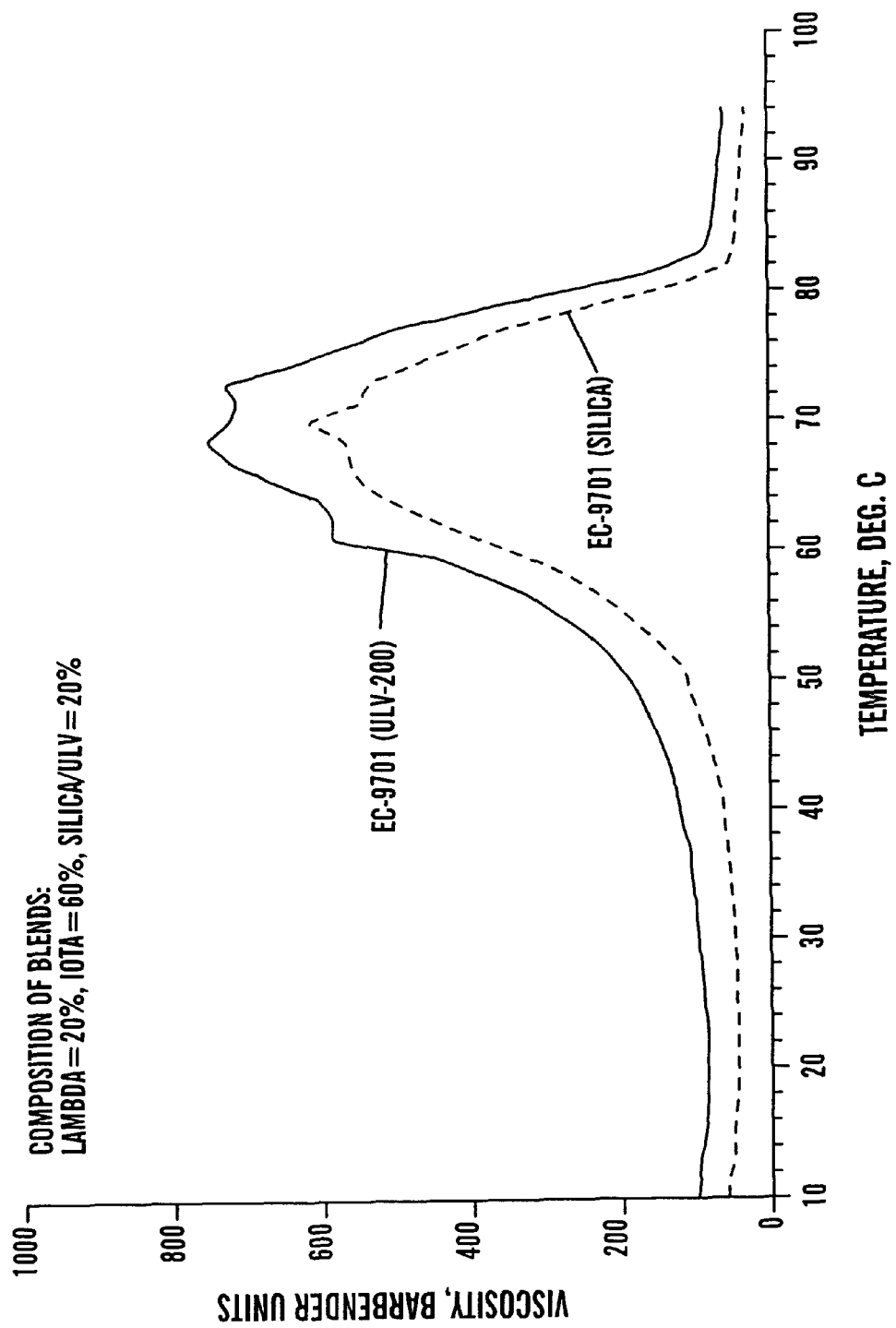
FIG. 4 is a diagrammatic representation of a hydration profile determination for 1) 20% lambda carrageenan, 60% iota carrageenan and 20% silica; and 2) 20% lambda carrageenan, 60% iota carrageenan and 20% ULV guar in a solution comprising 1:1 water:glycerin, 1% NaCl.

The hydration synergy observed with either iota or lambda carrageenan independently combined with ULV guar, (FIGS. 1 and 2, respectively) also occurred when a combination of iota and lambda types were combined with ULV guar. FIG. 4 shows hydration profiles for the preferred blend of iota and lambda carrageenan/ULV guar combination viscosity builder (labelled EC-9701 (ULV-200)) as compared to the hydration profile for an identical blend of carrageenans where the alternate binder silica has been substituted for ULV guar (labelled EC-9701 (silica)). The hydration profiles in FIG. 4 were generated using the following gum blend compositions under conditions of 2% gum, 1:1 water:glycerine, 1% sodium chloride.

| EC-9701 (ULV-200) | EC-9701 (silica) |
| --- | --- |
| 20% sodium lambda carrageenan | 20% sodium lambda carrageenan |
| 60% calcium iota carrageenan | 60% calcium iota carrageenan |
| 20% ULV guar 200 | 20% silica |

FIG. 4 demonstrates that the gum blend EC-9701 containing ULV guar generated higher viscosity than the gum blend containing the silica substitution, with the viscosity of the ULV-guar mix peaking at 770 Brabender units, and the silica mix peaking at 620 Brabender units. The synergy between carrageenan and ULV guar demonstrated in FIGS. 1 and 2, accounts for the enhanced hydration of the EC-9701 (ULV-200) formulation.

Table 2 compares the toothpaste viscosities determined for different toothpaste products made with either the combination ULV-guar/carrageenan (20% ULV-Guar/60% CI-100, 20% SL-100) viscosity builder of the current invention, or the currently marketed carrageenan (60% CI-100, 40% SL-100) viscosity builder.

|  | Dicalcium Phosphate Formula | | Chalk Formula | |
| --- | --- | --- | --- | --- |
|  | 25° C. | 48° C. | 25° C. | 48° C. |
| ULV-Guar/CI-100, SL-100 | | | | |
| Paste viscosity, BKU | 20.1 | 20.8 | 28.6 | 31.2 |
| cubans (@ 30 sec) | 6 | 6 | 8 | 9 |
| CI-100, SL-100 | | | | |
| Paste viscosity, BKU | 19.0 | 20.6 | 27.0 | 30.0 |
| cubans (@ 30 sec) | 6 | 6 | 8 | 8 |

This comparison indicates that toothpastes made with the combination viscosity builder of the current invention exhibit viscosity and strength comparable to the more expensive toothpastes whose formulas utilize higher concentrations of carrageenans.

We claim:

1. A combination viscosity builder for use in a toothpaste composition, the combination viscosity builder comprising ultra low viscosity guar and carrageenan.

2. The combination viscosity builder of claim 1, which, when included in a toothpaste composition, comprises less than about 10% of the toothpaste composition by weight.

3. The combination viscosity builder of claim 2, which, when included in a toothpaste composition, comprises about 0.5% to about 5% of the toothpaste composition by weight.

4. The combination viscosity builder of claim 1 wherein the low viscosity guar comprises less than about 50% of the combination viscosity builder by weight.

5. The combination viscosity builder of claim 4 wherein the low viscosity guar comprises from about 20% to about 30% of the combination viscosity builder by weight.

6. The combination viscosity builder of claim 1 wherein the low viscosity guar has a water viscosity rating of from about 200 cps to about 500 cps.

7. The combination viscosity builder of claim 6 wherein the low viscosity guar has a water viscosity rating of about 200 cps.

8. The combination viscosity builder of claim 1 wherein the carrageenan component comprises a mixture of iota and lambda carrageenan types.

9. The combination viscosity builder of claim 8 wherein the iota carrageenan type is produced as an approximately 100 mesh size calcium salt.

10. The combination viscosity builder of claim 8 wherein the lambda carrageenan type is produced as an approximately 100 mesh size sodium salt.

11. The combination viscosity builder of claim 1, which, when included in a toothpaste composition, produces an overall viscosity rating of the toothpaste between about 20–35 BKU.

12. The combination viscosity builder of claim 1, which, when included in a toothpaste, produces a paste strength between 6 and 9 as determined by Cuban rating.

13. A dry blend combination viscosity builder for use in a toothpaste composition, the dry blend comprising about 20–30% low viscosity guar, about 50–60% iota-type carrageenan and about 20–30% lambda-type carrageenan.

14. The dry blend of claim 13 wherein the low viscosity guar has a water viscosity rating of from about 200 cps to about 500 cps.

15. The dry blend of claim 14 wherein the low viscosity guar has a water viscosity rating of about 200 cps.

16. The dry blend of claim 13 wherein the iota carrageenan type is produced as an approximately 100 mesh size calcium salt.

17. The dry blend of claim 13 wherein the lambda carrageenan type is produced as an approximately 100 mesh size sodium salt.

18. The dry blend of claim 13, which when appropriately hydrated has a water viscosity rating of at least about 40 cps.

* * * * *